United States Patent
Stecher et al.

(10) Patent No.: US 12,173,214 B2
(45) Date of Patent: Dec. 24, 2024

(54) RARE EARTH NANOCRYSTAL FOR HIGHLY EFFICIENT NIR TO NIR WAVELENGTH CONVERSIONS

(71) Applicant: INTELLIGENT MATERIAL SOLUTIONS, INC., Princeton, NJ (US)

(72) Inventors: Joshua T. Stecher, Trenton, NJ (US); Howard Bell, Princeton, NJ (US); Joshua Collins, Wallingford, PA (US)

(73) Assignee: INTELLIGENT MATERIAL SOLUTIONS, INC, Princeton, NJ (US)

( * ) Notice: Subject to any disclaimer, the term of this patent is extended or adjusted under 35 U.S.C. 154(b) by 841 days.

(21) Appl. No.: 17/269,603

(22) PCT Filed: Aug. 21, 2019

(86) PCT No.: PCT/US2019/047397
§ 371 (c)(1),
(2) Date: Feb. 19, 2021

(87) PCT Pub. No.: WO2020/041402
PCT Pub. Date: Feb. 27, 2020

(65) Prior Publication Data
US 2021/0198570 A1 Jul. 1, 2021

Related U.S. Application Data

(60) Provisional application No. 62/272,275, filed on Aug. 21, 2018.

(51) Int. Cl.
| | | |
|---|---|---|
| C01F 17/36 | (2020.01) | |
| C09K 11/77 | (2006.01) | |
| G01N 33/58 | (2006.01) | |

(52) U.S. Cl.
CPC .......... *C09K 11/7773* (2013.01); *C01F 17/36* (2020.01); *G01N 33/582* (2013.01); *C01P 2002/52* (2013.01); *C01P 2002/82* (2013.01); *C01P 2004/04* (2013.01); *C01P 2004/82* (2013.01)

(58) Field of Classification Search
None
See application file for complete search history.

(56) References Cited

U.S. PATENT DOCUMENTS

| 9,181,477 B2 | 11/2015 | Collins et al. |
| 2015/0362432 A1 | 12/2015 | Han et al. |

FOREIGN PATENT DOCUMENTS

| CN | 103774221 A | 5/2014 |
| CN | 106867509 A | 6/2017 |
| CN | 107286924 A | 10/2017 |
| SG | 10201509100 | * 6/2016 |

OTHER PUBLICATIONS

Chen, et al. "Ultrasmall Monodisperse NaYF4:Yb/Tm Nanocrystals . . . ". American Chemical Society. vol. 4, No. 6, 3163-3168 (2010). (Year: 2010).*
International Search Report and Written Opinion for corresponding PCT Application No. PCT/US2019/047397, dated Nov. 1, 2019.
Ai, X et al. "Synthesis of Core-shell lanthanide-doped Upconversion Nanocrystals for Cellular Applications" Journal of Visualized Experiments, vol. 129, e56416, pp. 1-9, Nov. 2017.
Chen, et al. "Ultrasmall Monodisperse NaYF4:Yb3+/Tm3+ Nanocrystals with Enhanced Near-Infrared to Near-Infrared Upconversion Photoluminescence", ACS Nano, vol. 4, No. 6, pp. 3163-3168. May 28, 2010.
Himmelstoss, et al., "980 nm and 808 nm excitable upconversion nanoparticles for the detection of enzyme related reactions", Nanoscale Imaging, Sensing, and Actuation for Biomedical Applications XIV, SPIE vol. 10077, 100770L, pp. 1-6, 2017.

\* cited by examiner

*Primary Examiner* — Sheng H Davis
(74) *Attorney, Agent, or Firm* — MEAGHER EMANUEL LAKS GOLDBERG & LIAO, LLP

(57) ABSTRACT

Disclosed is a novel composition of matter that provides highly efficient energy conversion from NIR to NIR wavelengths, with either up-, down-, or both up- and down-converting transitions. Disclosed is a composition having the molecular formula $NaYF_4:Yb_xTm_yNd_z$, where $0 \leq x \leq 0.98$, $0 \leq y \leq 0.02$, and $0 \leq z \leq 0.06$. Also disclosed is a core-shell structure, wherein the core is a composition having the molecular formula $NaYF_4:Yb_xTm_yNd_z$, where $0 \leq x \leq 0.98$, $0 \leq y \leq 0.02$, and $0 \leq z \leq 0.06$, and the shell is composition having the molecular formula $NaYF_4:Nd_w$, where $0 \leq w \leq 0.1$.

4 Claims, 7 Drawing Sheets

RARE EARTH NANOCRYSTAL FOR HIGHLY EFFICIENT NIR TO NIR WAVELENGTH CONVERSIONS

CROSS-REFERENCE TO RELATED APPLICATIONS

This application claims priority to U.S. Provisional Application No. 62/720,275, filed on Aug. 21, 2018, which is hereby incorporated by reference in its entirety.

TECHNICAL FIELD

This invention relates generally to the phosphors, and more particularly, to phosphors providing highly efficient energy conversion from NIR to NIR wavelengths, with either up-, down-, or both up- and down-converting transitions.

BACKGROUND

Phosphor efficiency is an important metric in many phosphor applications. For example, the losses in a White Light Emitting Devices (WLEDs), such as those found in LED light bulbs, are typically the result of two sources after photons leave the LED chip: (1) a nonideal quantum efficiency for the phosphor ($\eta q$), and (2) a nonideal efficiency for the packaging of the device ($\eta p$). Conversion efficiency (CE) is the product of $\eta q$ and $\eta p$. Ideal products have a CE=1. The more energy that is required to reach a certain illumination, the more heat is generated, and high temperatures in the package can cause thermal quenching of the phosphor, leading to color drive, blue-light leakage, efficiency drop, and a shortened lifetime.

Further, in some instances, such as those relating to detecting the presence of particles, high efficiency is critical for being able to detect very low concentrations of the particles.

Thus, phosphors having a high efficiency are therefore highly desirable.

BRIEF SUMMARY

Disclosed is a composition of matter capable of highly efficient NIR to NIR wavelength conversions, having the molecular formula $NaYF_4:Yb_xTm_yNd_z$, where $0 \leq x \leq 0.98$, $0 \leq y \leq 0.02$, and $0 \leq z \leq 0.06$. In some embodiments, $0 < x \leq 0.98$, $0 < y \leq 0.02$, and $0 < z \leq 0.06$. In some embodiments, $0.6 \leq x \leq 0.8$, $0 < y \leq 0.02$, and $z=0$. In some embodiments, $0 < y \leq 0.02$, $x=0$, and $z=0$. In some embodiments, $0.01 \leq x \leq 0.07$, $y=0$, and $0.01 \leq z \leq 0.05$. In some embodiments, the molecular formula is $NaYF_4:Yb_{0.7}Tm_{0.02}$, $NaYF_4:Tm_{0.02}$, $NaYF_4:Yb_{0.05}Nd_{0.03}$, or $NaYF_4:Yb_{0.1}Nd_{0.02}Tm_{0.01}$.

The disclosed composition of matter may be incorporated as part of a core-shell arrangement, where the core comprises the disclosed composition of matter, and the shell is either undoped $NaYF_4$ or has a molecular formula $NaYF_4:Nd_w$, where $0 \leq w \leq 0.1$. Optionally, the core has a molecular formula $NaYF_4:Tm_{0.02}$, and the shell is either $NaYF_4:Nd_{0.05}$ or $NaYF_4:Nd_{0.10}$. Optionally, the core has a molecular formula $NaYF_4:Yb_{0.1}Nd_{0.02}Tm_{0.01}$, and the shell is undoped $NaYF_4$.

The disclosed composition of matter may be used to detect an analyte. The method for doing so includes providing a sample that is believed to include an analyte, then providing a conjugate of the disclosed composition of matter and allowing the conjugate to attach to any analyte. After removing a non-attached conjugate, the sample can be irradiated with at least one first wavelength, the phosphor will emit at least one second wavelength different from the at least one first wavelength, and the emitted second wavelength(s) can be detected.

DETAILED DESCRIPTION

Figure 1A:
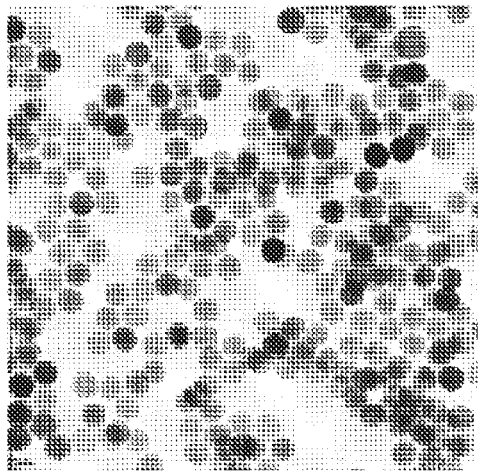
FIGS. 1A-1D are TEM images of an embodiment of a composition capable of up-conversion and down-conversion, having the molecular formula $NaYF_4:Yb_{0.7}Tm_{0.02}$, with various mean particle diameters—30 nm (FIG. 1A), 75 nm (FIG. 1B), 150 nm (FIG. 1C), and 190 nm (FIG. 1D).
Figure 1B:
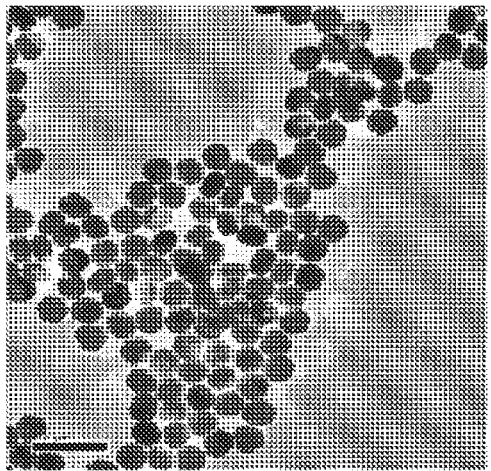
Figure 1C:
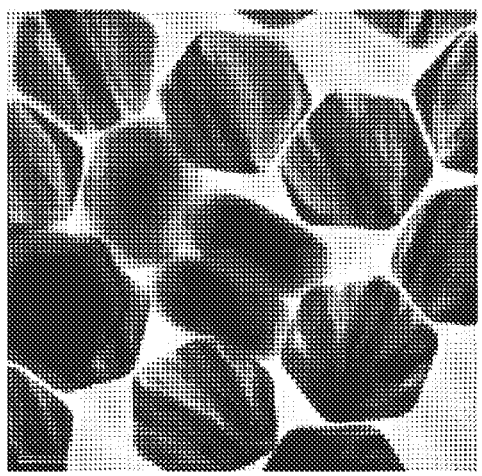

Disclosed are compositions showing significant improvements in conversion efficiency compared to conventional doping ratios and nanoparticle architectures, as well as the ability to provide both up and down-conversion properties in a single nanocrystal composition.

The disclosed composition of matter has a molecular formula $NaYF_4:Yb_xTm_yNd_z$, where $0 \leq x \leq 0.98$, $0 \leq y \leq 0.02$, and $0 \leq z \leq 0.06$. In some embodiments, $z=0$. In some embodiments, $0.6 \leq x \leq 0.8$, $0 < y \leq 0.02$, and $z=0$. In some embodiments, x=0 and z=0. In some embodiments, x, y, and z are each greater than 0. In some embodiments, at least y is greater than 0. In some embodiments, y=0. In some embodiments, $0.01 \leq x \leq 0.07$, y=0, and $0.01 \leq z \leq 0.05$. Exemplary molecular formulas include, but are not limited to, $NaYF_4$: $Yb_{0.7}Tm_{0.02}$, $NaYF_4$:$Tm_{0.02}$, $NaYF_4$:$Yb_{0.05}Nd_{0.03}$, or $NaYF_4$:$Yb_{0.1}Nd_{0.02}Tm_{0.01}$.

Mean particle diameters of the disclosed compositions of matter are typically less than 1 μm. Preferred embodiments have mean diameters less than or equal to 200 nm. More preferred embodiments have mean diameters less than or equal to 100 nm. Still more preferred embodiments have mean particle diameters less than 50 nm.

The disclosed composition of matter can also be used to create a core-shell structure. The core may have the molecular formula $NaYF_4$:$Yb_xTm_yNd_z$, where $0 \leq x \leq 0.98$, $0 \leq y \leq 0.02$, and $0 \leq z \leq 0.06$. The shell may be either undoped $NaYF_4$ or $NaYF_4$ doped with a relatively small amount of Neodymium (Nd). That is, the shell may be a composition having the molecular formula $NaYF_4$:$Nd_w$, where $0 \leq w \leq 0.1$.

The disclosed compositions have been synthesized using methods known to those of skill in the art, including those disclosed in U.S. Pat. No. 9,181,477, which is incorporated by reference herein in its entirety. Such methods can be used to yield highly uniform nanocrystals with tunable sizes and morphologies, as shown in the TEM images shown in FIGS. 1A-D, 2, 3A-B, 4A, 5A-C, and 6A-6B.

An example process can be described as follows. For some embodiments, a precursor metal salt, or a mixture of precursor metal salts, is dissolved in a solvent to form a solution in a reaction vessel. The reaction vessel is then placed in a heated salt bath having a temperature of at least about 340° C. Heat is applied to the salt bath to rapidly decompose the precursor metal salts in the solution to form the monodisperse particles. The reaction vessel is then kept in the salt bath for a time sufficient to increase the size of the monodisperse particles to a desired size. The reaction vessel is then removed from the salt bath; and the reaction quenched with ambient temperature solvent.

The particles of the invention are synthesized through thermal decomposition of precursor metal salts of the desired particle composition components. One of ordinary skill in the art would know the precursor salts which may be used to yield a particular particle composition. The desired stoichiometric combination of precursor metal salts may be first dissolved in a solvent to form a solution of the precursor compounds, for example in a 100 mL, 3-neck flat-bottom flask. Suitable solvents include, but are not limited to, a mixture of oleic acid and 1-octadecene, oleylamine, trioctylamine, trioctylphosphine, squalene, trioctylphosphine oxide, hexadecylamine, and the like, which are typically solids at room temperature. A preferred solvent for the synthesis of monodisperse particles of the invention is a mixture of oliec acid and 1-octadecene.

In some embodiments, the oleic acid and 1-octadecene may be mixed in a 1:1 ratio. The mixture is typically heated under vacuum at 100° C. to dissolve the trifluoracetate salts and remove excess water. The reaction vessel containing the hot mixture is preferably purged with an inert gas such as nitrogen. The vessel is then placed in a molten salt bath while still purging with the inert gas. The salt bath should have a temperature of at least about 340° C. Salt baths known in the art may be used, with a 1:1 $KNO_3$/$NaNO_3$ salt bath being preferred. The salt bath acts as the heat reservoir to ensure the fast and uniform heating of the solution and also to compensate the disparity in decomposition temperature among various trifluoroacetate salts. The temperature of the salt bath should be maintained throughout the entire reaction. Once the reaction is complete, the vessel is removed from the salt bath and the reaction quenched with room temperature solvent and the reaction stopped. In the case of a solvent mixture, such as oleic acid and 1-octadecene, one or both components can be used—for oleic acid/1-octadecenc, 1-octdecene may preferably be added to quench the reaction. The product particles may then be precipitated by addition of an antisolvent, such as ethanol, and recovered by means known in the art such as centrifugation, filtration, etc. The particles may be washed by resuspending them in a non-polar solvent such as hexane, recovered, and dried at room temperature, with heat, and/or with vacuum.

When oleic acid/1-octadecene is used as the solvent, it has been observed using FTIR that some oleic acid attaches to the particle surface during the reaction, although subsequent washings of the particles can remove oleic acid. This is presumably due to the carboxylic acid functional group in the oleic acid. Conducting the reaction in the presence of solvents having such functional groups which may attach to the surface of the monodisperse particles, or adding such compounds to the reaction, then is one route to introduce functionality to the particle surface. In the case of oleic acid, although not to be bound by theory, it is believed that the oleic acid acts as a surfactant, assisting in the coordination of the precursor lattice framework. Under high temperature, oleic acid molecules form ionic bonds between the carboxyl group of the oleic acid and the RE ions in the crystal lattice. The oleic acid functionalization also is believed to assist in suspending the monodisperse particles of the invention in hexane or other non-polar solvents and in their self-assembly into superlattices. Monodisperse particles of the invention having oleic acid surface modification represent another embodiment of the invention.

Particle size and morphology may be controlled by varying reaction conditions such as stoichiometric precursor metal salt ratio, heating rate of the salt bath, and reaction time. The initial rate of heating in the salt bath is important in determining the morphology by selecting which crystal planes will undergo the most rapid growth. Final particle size is determined by total reaction time in the salt bath as well as precursor ratios. After the reaction vessel reaches the temperature of the salt bath, the longer the time the vessel remains in the salt bath the larger the particles may grow.

The disclosed compositions and core-shell structures show significant conversion efficiency improvement compared to conventional doping ratios and nanoparticle architectures. Further, one embodiment provides both up and down-conversion properties in a single nanocrystal composition.

Example 1

Figure 1D:
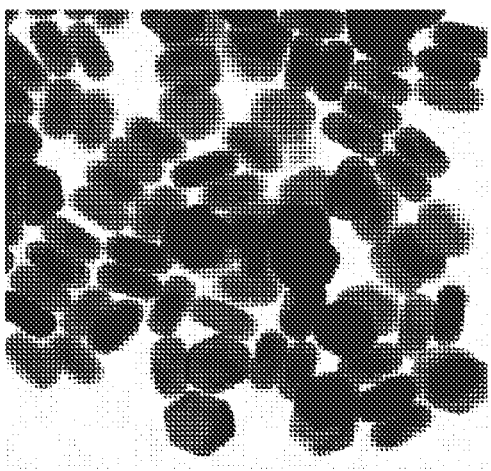
Figure 1E:
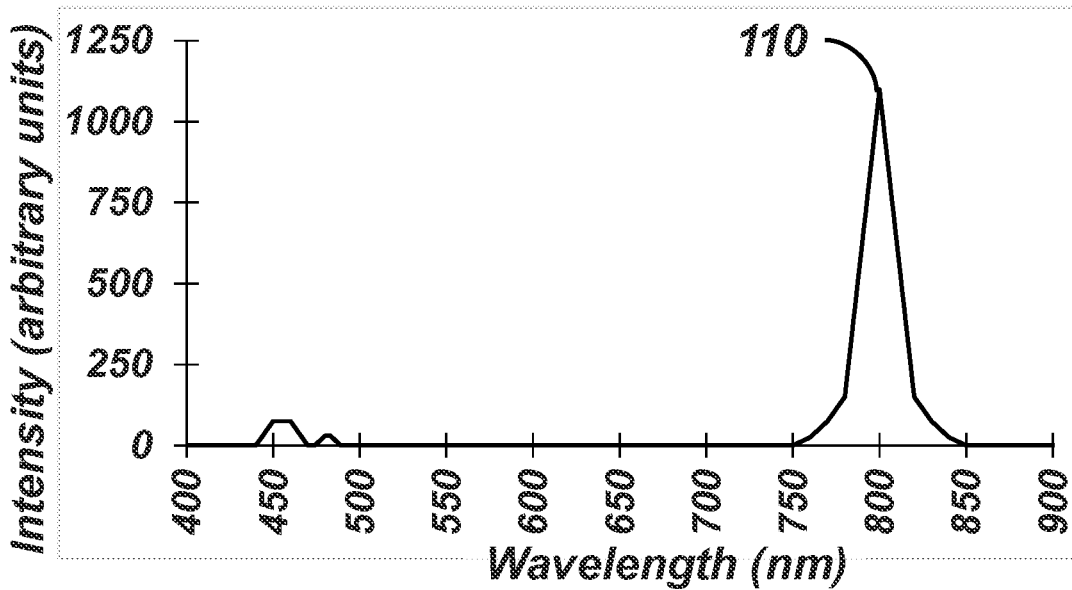
FIG. 1E is a graph illustrating a sample spectral data of the NIR to NIR up-conversion (980 nm to 800 nm) of the composition having the molecular formula $NaYF_4:Yb_{0.7}Tm_{0.02}$.

A first example is described by the chemical formulation $NaYF_4$:$Yb_{0.7}Tm_{0.02}$. Various images of this composition can be seen in FIGS. 1A-1D, having different mean particle diameters, including 30 nm (FIG. 1A), 75 nm (FIG. 1B), 150 nm (FIG. 1C), and 190 nm (FIG. 1D). This example is typically utilized for NIR to NIR up-conversion. As seen in reference to FIG. 1E, this composition upconverts from 980 nm to 800 nm (110).

Figure 1F:
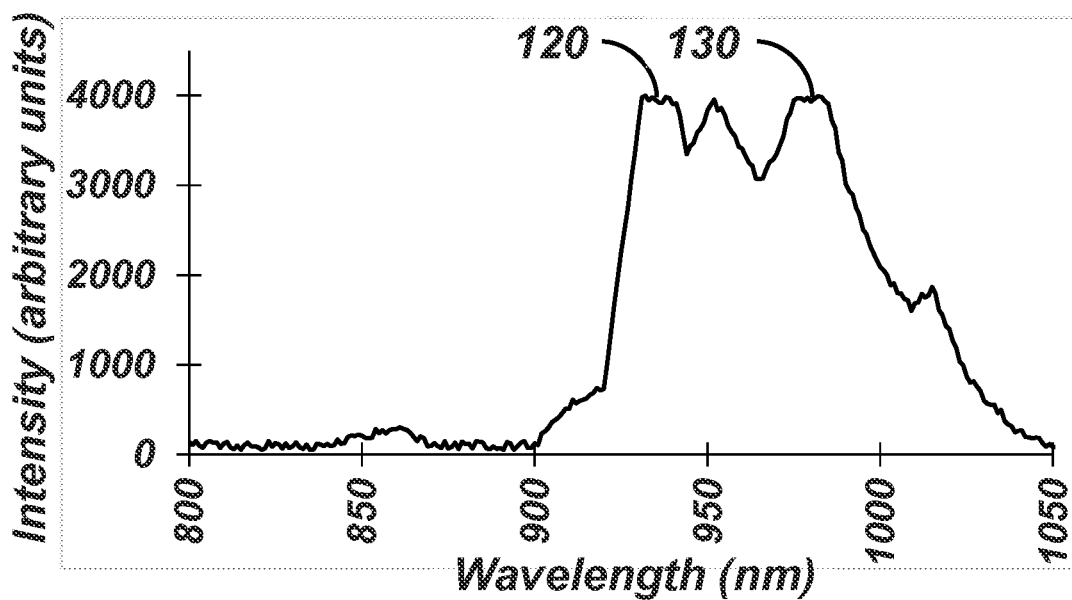
FIG. 1F is a graph illustrating a sample spectral data of the NIR to NIR down-conversion (940 nm to 980 nm) of the composition having the molecular formula $NaYF_4:Yb_{0.7}Tm_{0.02}$.
Figure 2:
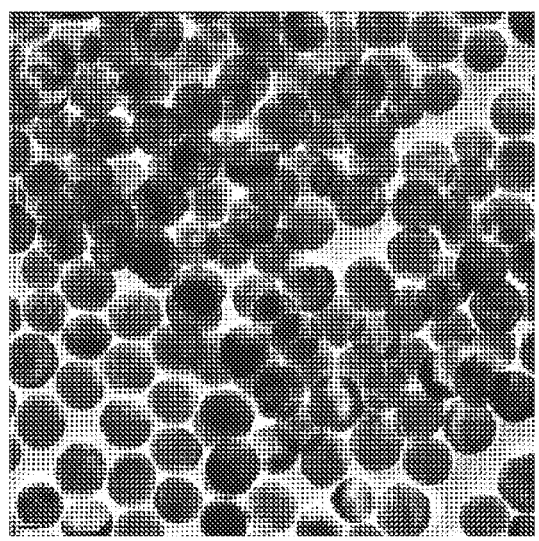
FIG. 2 is a TEM image of an embodiment of a composition capable of up- and down-conversion, having the molecular formula $NaYF_4:Tm_{0.02}$, with a 50 nm mean particle diameter.

This example also possesses a unique down-conversion transition from 940 nm to 980 nm shown in FIG. 1F. As seen in reference to FIG. 1F, this example also exhibits a down-conversion from a 940 nm (120) to 980 nm (130).

Example 2

A second example is described by the chemical formulation $NaYbF_4:Tm_{0.02}$. Images of this composition can be seen in FIG. 2. This embodiment is typically utilized for NIR to NIR up/down-conversion.

Example 3

Figure 3A:
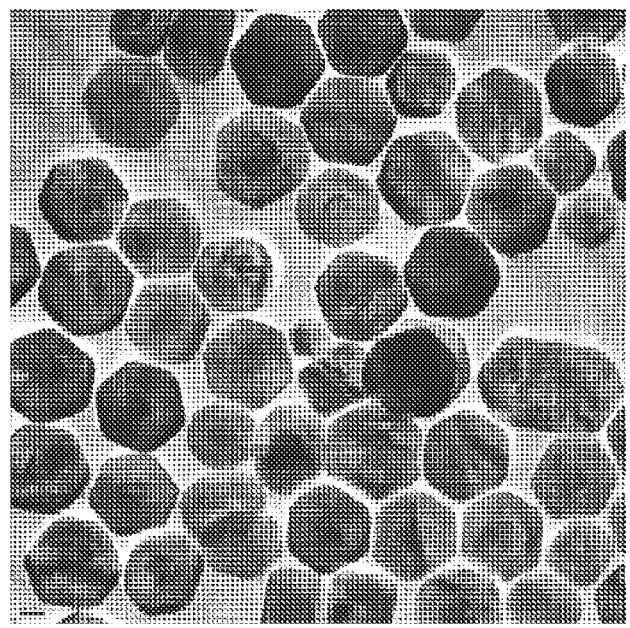
FIG. 3A is a TEM image of an embodiment of a composition capable of up- and down-conversion, with 75 nm mean particle diameter core-shell particles, where the core has a molecular formula of $NaYF_4:Tm_{0.02}$ and the shell has a molecular formula of $NaYF_4:Nd_{0.05}$.
Figure 3B:
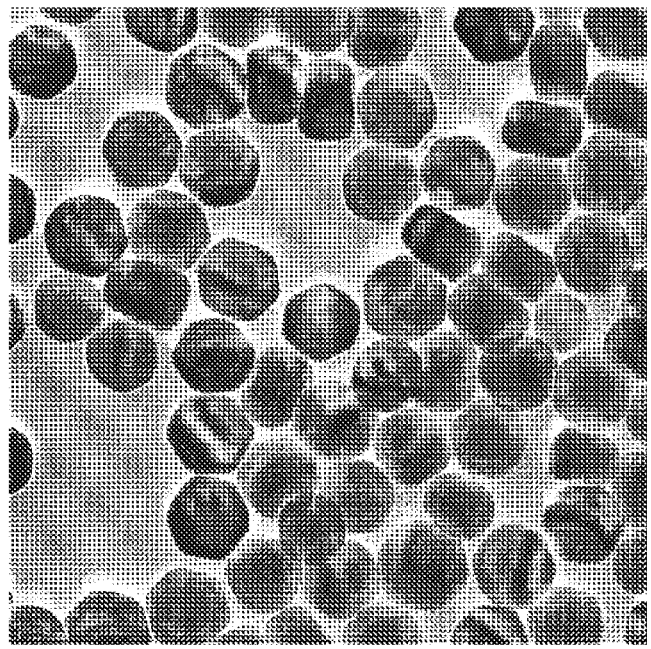
FIG. 3B is a TEM image of an embodiment of a composition capable of up- and down-conversion, with 75 nm mean particle diameter core-shell particles, where the core has a molecular formula of $NaYF_4:Tm_{0.02}$ and the shell has a molecular formula of $NaYF_4:Nd_{0.10}$.

Example core-shell constructions are shown in FIGS. 3A and 3B. FIG. 3A depicts an up/down conversion system with a core composed of having $NaYbF_4:Tm_{0.02}$, and a shell composed of $NaYF_4:Nd_{0.05}$. FIG. 3B depicts an up/down conversion system with a core composed of having $NaYbF_4:Tm_{0.02}$, and a shell composed of $NaYF_4:Nd_{0.10}$.

Example 4

Figure 4A:
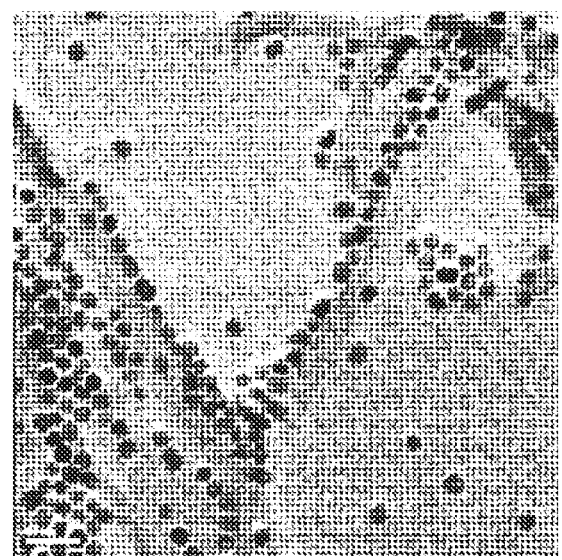
FIG. 4A is a TEM image of an embodiment capable of NIR to NIR down-conversion, having the molecular formula $NaYF_4:Yb_{0.05}Nd_{0.03}$.
Figure 4B:
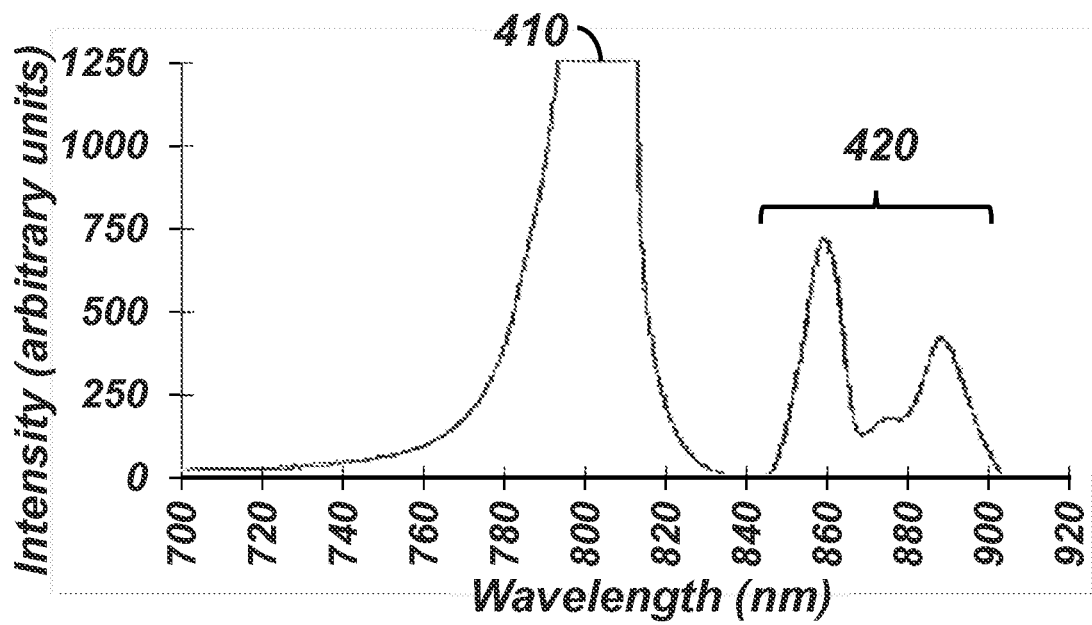
FIG. 4B is a graph illustrating a sample spectral data of the NIR to NIR down-conversion (808 nm to 850-900 nm) of the composition having the molecular formula $NaYF_4:Yb_{0.05}Nd_{0.03}$.

A fourth example is described by the chemical formulation $NaYF_4:Yb_{0.05}Nd_{0.03}$. TEMs of this composition can be seen in FIG. 4A. Spectral data for this composition is shown in FIG. 4B, where the 808 nm excitation peak (410) can be seen next to the 850-900 nm emission peaks (420). This embodiment is typically utilized for NIR to NIR Down-conversion.

Example 5

Figure 5A:
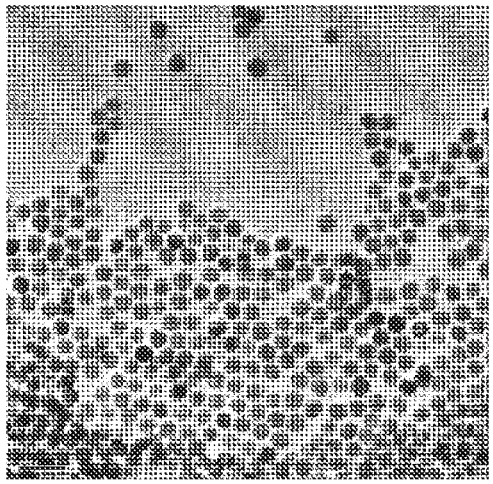
FIGS. 5A-5C are TEM images of an embodiment of a composition capable of up-conversion, having the molecular formula $NaYF_4:Yb_{0.1}Nd_{0.02}Tm_{0.01}$, with various mean particle diameters—15 nm (FIG. 5A), 20 nm (FIG. 5B), and 200 nm (FIG. 5C).
Figure 5B:
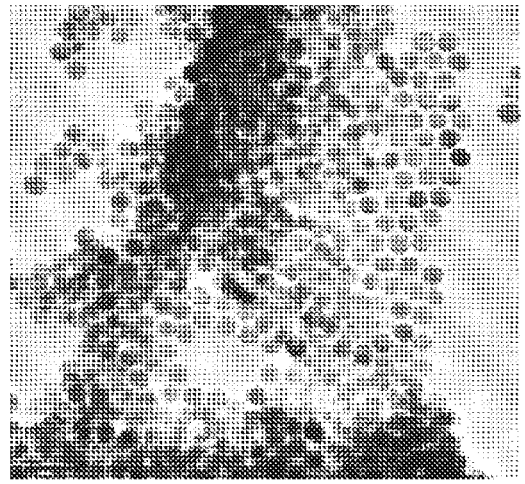
Figure 5C:
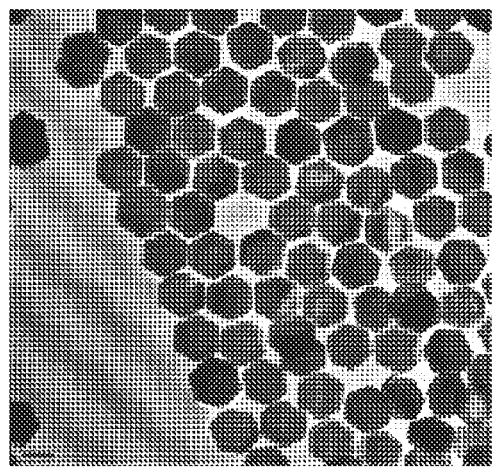

A fifth example is described by the chemical formulation $NaYF_4:Yb_{0.1}Nd_{0.02}Tm_{0.01}$. Various TEM images of this composition can be seen in FIGS. 5A-5C, each with a different mean particle diameter—15 nm (FIG. 5A), 20 nm (FIG. 5B), and 200 nm (FIG. 5C). This embodiment is typically utilized for NIR to NIR up/down-conversion.

Example 6

Figure 6A:
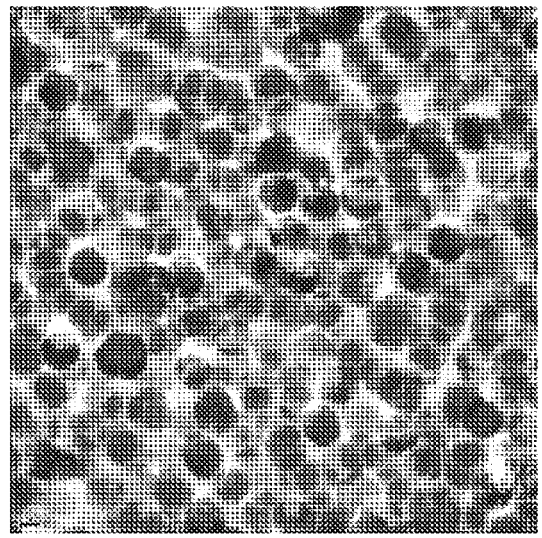
FIG. 6A is a TEM image of an embodiment of a composition capable of down-conversion, with 40 nm mean particle diameter core-shell particles, where the core has a molecular formula of $NaYF_4:Yb_{0.1}Nd_{0.02}Tm_{0.01}$ and the shell has a molecular formula of $NaYF_4$.
Figure 6B:
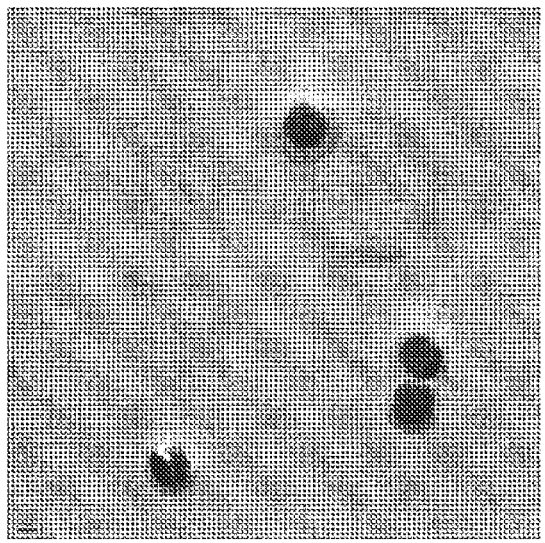
FIG. 6B is a TEM image of an embodiment of an undoped shell, having a molecular formula of $NaYF_4$, with 40 nm mean particle diameter.

A sixth example, illustrating core-shell constructions are shown in FIGS. 6A and 6B, which depicts a down conversion system with a core composed of having $NaYF_4:Yb_{0.1}Tm_{0.01}Nd_{0.02}$, and a shell composed of undoped $NaYF_4$.

The composition can be utilized in a variety of assays such as lateral flow or microfluidic based sandwich immunoassays, competition assays, homogeneous and direct bind assays for application in flow cytometry. An assay using the disclosed composition can be easily modified to analyze a variety of sample specimens and target analytes, which are typically extracted or concentrated from the sample specimens. Test samples can be derived from humans and include saliva, whole blood, serum, urine, other bodily fluids and tissues. Plant samples can be obtained from leaf, stem, phloem, cambium, xylem, flower, and heartwood. Other sample analytes and applications can include water, veterinary including livestock, and other consumer produce.

As an example, $NaYF_4:Yb_{0.7}Tm_{0.02}$ may be surface modified via available ligand exchange methodologies, with, e.g., a carboxylic acid and/or amine group which may then conjugated via amide bond formation (although other linker chemistry may also be used) to a target antibody, oligo, peptide, or nanobody of choice. The conjugated rare earth nanoparticle can be utilized in a sandwich immunoassay by three different approaches.

One approach is a single-step Flow Process. The nanoparticle conjugate is mixed with a sample specimen such as whole blood, saliva, urine, serum, etc. (purified or un-purified). The nanoparticle conjugate will bind to any biomarker targets present in the sample. The incubated sample is then applied to a nitrocellulose membrane at which point the sample containing nanoparticle conjugates and target flows across the membrane via capillary action. Any nanoparticle conjugate/target complexes will be captured by 'capture' antibodies at pre-printed sites along the nitrocellulose membrane that will be read by the scanner.

Another approach is a Consecutive Flow Process. The sample containing target species is applied first to the nitrocellulose membrane allowing the biomarker targets to be captured at the capture antibody sites. The nanoparticle conjugate is then applied to the nitrocellulose pad and flowed down the pad to attach to any target present and captured at the pre-printed sites. The tagged sites are then interrogated by an optical scanning device.

In a third approach, the nanoparticle conjugates are lyophilized in a storage media on the conjugate release pad or well located on the nitrocellulose strip. The sample specimen containing the target biomarkers are applied to the nitrocellulose membrane where the buffer solution is used to re-constitute the lyophilized nanoparticle conjugates and allowed to mix with the target biomarker, labelling the targets with the nanoparticle conjugate then flowing the buffer solution containing the nanoparticle conjugate/target complex that then binds to the pre-printed capture antibodies on the nitrocellulose membrane. The optical scanner is then used to interrogate the sites.

Thus, the method for detecting an analyte can be generally understood to require providing an analyte, either by itself or within a sample or carrier fluid. A conjugate of one of the disclosed compositions is also provided, where the conjugate is configured to bind to the analyte of interest. The conjugate is then allowed to bind to the analyte (typically by allowing the sample or carrier fluid containing the analyte to mix with the conjugate, flow over the conjugate, or otherwise chemically interact with the conjugate). Any non-attached conjugate is then removed in a manner known to those of skill in the art. At this point, the analytes are bound to the conjugates, and substantially no additional unattached conjugates remain (typically below limit of detection, or insufficient quantities to significantly alter any scan results). The attached conjugates are irradiated with at least one first wavelength of light, such that the disclosed compositions absorb the irradiation, and emit at least one second wavelength that is different from the first wavelength. That at least one second wavelength can be detected and measured, and, a value representing the concentration of the analyte in the sample can be determined based on that measured second wavelength. For example, a predetermined calibration curve can be used to convert to a concentration. In another example, the concentration of a target analyte can be determined by comparing the signal received from the conjugate attached to the target analyte to the signal received from a different conjugate attached to a second analyte with a known concentration (e.g., concentration of target analyte=signal from target analyte/signal from known analyte x concentration of known analyte).

Various other examples are described below.

Infectious & other Acute & Chronic Disease. A field-friendly screening tool has been developed for simplifying serological diagnosis of infectious disease. Various examples of assays utilizing the described composition show the highest sensitivity assay compared to ELISA, gold immunoassays, and other fluorescent dyes in the detection of Neurocysticercosis (Schistosoma), Tuberculosis, Leprosy, Dengue, and other infectious diseases. Other disease diagnostics can be monitored such as markers for cardiac stress, inflammatory diseases, among other disease processes.

Traumatic Brain Injury. Traumatic brain injury (TBI) affects nearly 1.7 million people each year, highlighting the need for a non-invasive, rapid diagnostic assay to identify and quantify the many biomarkers associated with mild to severe TBI. The compositions of matter can be utilized in a field deployable assay for the rapid diagnosis of TBI. Serum biomarkers GFAP, UCH-L1, LPA, S-100β, PrP$^c$, Phospho-Tau, and Total Tau have been identified. Having a rapid diagnostic will enable prediction of functional outcomes and advisement on return to play/work protocols for sports or work before resuming any activity. The unique ability of the disclosed nanocrystals to upconvert light as well as possess unique and tunable lifetime properties makes them superior to any other assay in regard to sensitivity, cost, and time to result. The ability to achieve high levels of multiplexing through lifetime tuning enables high throughput processing of samples and high accuracy readings. Other areas of applicability for this assay family is for other dementia or neurodegenerative related disorders including Alzheimer's, Parkinson's, Huntington's Disease.

CBRNE. Early detection or identification of biological warfare and prompt diagnosis of ensuing infections are critical to minimizing population effects and are essential components of biodefense using a rapid field diagnostic for the detection and quantification of exposure to various CBRNE compounds such as radiation, nerve agent, and anthrax.

Agriculture. HLB (Huanglongbing) is wreaking havoc on citrus globally and the potential commercial impact on growers threatens the future of the industry. Unfortunately, physical symptoms presented by HLB infected trees often are similar to other diseases and other plant stresses. This challenge makes it difficult for growers to quickly and accurately diagnose and take appropriate action. The disclosed composition of matter can be used with a field-appropriate detection platform for agricultural diseases as well as for monitoring the microbiome of the plant. The high sensitivity of the disclosed nanocrystal reporters and portable detection hardware provide specific optical signals with no background noise.

H2O Testing. Growing levels of contaminants, pathogens and pollutants have prompted the need for immediate detection, plus a more rigorous monitoring of surface and groundwater. The composition of matter can be utilized with water quality assurance platforms designed for detection of a wide range of contaminants including: heavy metals from aging water pipes and infrastructure, chemicals from industrial and agricultural effluent entering rivers and aquifers, hormones and prescription chemicals from domestic waste water, errant bacteria from waste management and water recovery, river and lake sediments after flooding.

Typically, competition assays will be used to identify presence of heavy metals in water by monitoring the decrease in emission intensity of the nanocrystals when chelated to a heavy metal. Chelation chemistries can include glutathiones, cysteines, and other tripeptide moieties.

A system using the disclosed nanocrystals may be an automated, simple-to-use platform that can detect a library of biological and chemical contaminants in residential and industrial settings. The system will typically utilize a light source and a detector in a housing, along with a processor for controlling the light source and detector. The system may be connected to other devices (including cloud-based storage or servers) via wired or wireless connections. The system would utilize conjugated versions of the disclosed compositions to capture target analytes, and then use the light source and detectors to determine concentrations.

Other platforms, based on, e.g., Mid Infrared Spectroscopy, may also use the disclosed nanocrystals detect of chemical contaminants in water such as arsenic, atrazine, and nitrates. The modular nature of the disclosed nanocrystals allows for rapid tailoring of the detection platform to meet local needs.

Examples of detector assay sample readouts can be multi-well plate or microarray, microfluidic, nitrocellulose and PVDF or similar capillary flow membranes, and other formats for sandwich or competitive immunoassays. The platform for water quality testing will be semi-automated and test. These assays can be easily adapted for both field deployable or point-of-care testing or in high throughput industrial applications.

What is claimed is:

1. A core-shell structure consisting of:
   a core comprising a composition of matter having the molecular formula NaYF$_4$: Yb$_x$Tm$_y$Nd$_z$, wherein 0≤x≤0.98, 0≤y≤0.02, and 0≤z≤0.06; and
   a shell that has a molecular formula NaYF$_4$: Nd$_w$, where 0≤w≤0.1;
   wherein:
   the core has a molecular formula of NaYF$_4$: Yb$_{0.1}$Nd$_{0.02}$Tm$_{0.01}$;
   the core has a molecular formula of NaYF$_4$: Yb$_{0.7}$Tm$_{0.02}$;
   the core has a molecular formula of NaYbF$_4$: Tm$_{0.02}$; or
   the core has a molecular formula of NaYF$_4$: Yb$_{0.05}$Nd$_{0.03}$.

2. The core-shell structure according to claim 1, wherein the core has a molecular formula NaYbF$_4$: Tm$_{0.02}$, and the shell has a molecular formula NaYF$_4$: Nd$_{0.05}$ or NaYF$_4$: Nd$_{0.10}$.

3. The core-shell structure according to claim 1, wherein the core has a molecular formula NaYF$_4$: Yb$_{0.05}$Nd$_{0.03}$, and the shell is undoped NaYF$_4$.

4. A core-shell structure consisting of:
   a core comprising a composition of matter having the molecular formula NaYF$_4$: Yb$_x$Tm$_y$Nd$_z$, wherein 0.01≤x≤0.07, y=0, and 0.01≤z≤0.05; and
   a shell that has a molecular formula NaYF$_4$: Nd$_w$, where 0≤w≤0.1.

* * * * *